US012633402B2

(12) United States Patent
John et al.

(10) Patent No.: US 12,633,402 B2
(45) Date of Patent: May 19, 2026

(54) METHOD, APPARATUS, AND COMPUTER-READABLE MEDIUM FOR SCHEDULING PROCEDURES IN A HOSPITAL

(71) Applicant: Fraunhofer-Gesellschaft zur Förderung der angewandten Forschung e.V., Munich (DE)

(72) Inventors: Ole John, Hamburg (DE); Anisa Rizvanolli, Hamburg (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 167 days.

(21) Appl. No.: 18/393,707

(22) Filed: Dec. 22, 2023

(65) Prior Publication Data

US 2025/0210183 A1      Jun. 26, 2025

(51) Int. Cl.
  G16H 40/20       (2018.01)
  G16H 40/40       (2018.01)

(52) U.S. Cl.
  CPC ............. G16H 40/20 (2018.01); G16H 40/40 (2018.01)

(58) Field of Classification Search
  CPC ............................... G16H 40/20; G16H 40/40
  See application file for complete search history.

(56) References Cited

U.S. PATENT DOCUMENTS

| | | | |
|---|---|---|---|
| 8,725,547 B2 * | 5/2014 | Fuhrmann | G16Z 99/00 |
| | | | 705/2 |
| 2023/0011342 A1 * | 1/2023 | Dewan | G16H 10/60 |

FOREIGN PATENT DOCUMENTS

| | | | |
|---|---|---|---|
| DE | 102018216514 A1 | 3/2020 | |
| EP | 2063373 A1 * | 5/2009 | ............. G16H 20/40 |

OTHER PUBLICATIONS

Schouten, Anne M. et al. "Operating Room Performance Optimization Metrics: a Systematic Review." Journal of Medical Systems, 47(1), Article 19. https://doi.org/10.1007/s10916-023-01912-9. Accepted: Nov. 26, 2022. Published online Feb. 4, 2023 (Year: 2022).*

* cited by examiner

*Primary Examiner* — Linh Giang Le
(74) *Attorney, Agent, or Firm* — 2SPL Patentanwälte; Kieran O'Leary

(57)                ABSTRACT

A method, apparatus, and non-transitory, computer readable medium for scheduling a plurality of procedures in a hospital. The method interfaces with a network of the hospital to acquire resource information by monitoring a plurality of hospital resources, obtain procedure information, and access personnel information. The plurality of hospital resources includes a plurality of rooms and medical devices and the personnel information includes qualifications and working hours. The method further includes processing the resource information, procedure information, and personnel information to generate one or more hospital schedules using a model based on a predetermined parameter hierarchy and modified based on a hardness quotient. The hospital schedule assigns an at least one room, medical device, and personnel for each procedure. The method then ranks the hospital schedules and interfacing with the network of the hospital to electronically reserve the rooms and electronically prepare the medical devices based on a ranked hospital schedule.

23 Claims, 3 Drawing Sheets

METHOD, APPARATUS, AND COMPUTER-READABLE MEDIUM FOR SCHEDULING PROCEDURES IN A HOSPITAL

FIELD

Examples relate to a method, apparatus, and non-transitory, computer readable medium for scheduling a plurality of procedures in a hospital using a scheduling system.

BACKGROUND

It is often time-consuming to create a schedule of procedures in a hospital that has proper personnel deployment, operating room utilization, considers all necessary resources (such as operating equipment) and follows requirements set by the hospital and other regulatory authorities. This complex planning task can be described as an optimization problem for the optimal assignment of personnel, space, and medical device resources to an operation sequence, that can include both past and future situations. Current models, solutions, methods, and tools are currently lacking in this area. Therefore, an improved apparatus and method for automatically optimizing hospital planning is desired.

SUMMARY

An example relates to a method of scheduling a plurality of procedures in a hospital using a scheduling system including a processor and an interface. The method includes interfacing with a network of the hospital to acquire resource information by monitoring a plurality of hospital resources, obtain procedure information for a plurality of patients, and access personnel information on a plurality of personnel. The plurality of hospital resources includes a plurality of rooms and a plurality of medical devices and the personnel information includes qualifications and working hours for each personnel. The method further includes processing the resource information, procedure information, and personnel information to generate one or more hospital schedules using a model based on a predetermined parameter hierarchy. The hospital schedule assigns an at least one room, an at least one medical device, and an at least one personnel for each procedure and the model is modified based on a hardness quotient. The method further includes ranking the one or more hospital schedules according to the model' and interfacing with the network of the hospital to electronically reserve the rooms and electronically prepare the medical devices based on a ranked hospital schedule.

According to another example, the method further comprises presenting the one or more hospital schedules to a user, wherein the ranked hospital schedule is selected by the user.

According to another example, each procedure has a delay probability and wherein the model is further based on the delay probability of each procedure.

According to another example, the procedure information comprises a timeslot parameter for each procedure and the delay probability alters the timeslot parameter of each procedures.

According to another example, the hardness quotient modifies the model to produce one or more hospital schedules with increased availability parameters.

According to another example, the plurality of rooms comprises a first room subset and a second room subset and plurality of personnel comprises a first personnel subset, wherein resource information includes availability information on the first room subset and the second room subset and personnel information comprises availability information on the first personnel subset. Wherein the hardness quotient is between a combination of the availability information for the first room subset and the second room subset and the availability information for the first personnel subset. Wherein the predetermined parameter hierarchy is modified by the hardness quotient.

According to another example, the first room subset is operating rooms, the second room subset is e.g. anesthesia induction rooms, and the first personnel subset is e.g. anesthetists.

According to another example, the plurality of rooms comprises anesthesia induction rooms and wherein the plurality of personnel comprises anesthetists wherein the hardness quotient comprises a ratio between the availability information on a plurality of further rooms and the anesthesia induction rooms or anesthetists.

According to another example, the method further comprises interfacing with the network of the hospital to acquire updated resource information by monitoring the plurality of hospital resources to detect conflicts between the hospital schedule and the plurality of hospital resources. The method further comparing the hospital schedule with the updated resource information to detect deviations between the hospital schedule and the hospital resources, generate an updated hospital schedule in response to the detected deviations, wherein the updated hospital schedule is generated using the model. The method further interfacing with the network of the hospital to electronically reserve the rooms and electronically prepare the medical devices based on the updated hospital schedule.

According to another example, the hospital schedule comprises a task schedule for the personnel and a preparation schedule for the rooms and medical devices.

According to another example, the predetermined parameter hierarchy includes patient priority parameters, resource availability parameters, and personnel availability parameters. Wherein the model is further based on maintenance times for the medical devices so that the preparation schedule for the equipment indicates maintenance times. Wherein the model is further based on working hours for the personnel so that the task schedule for the personnel indicates working hours.

According to another example, the parameters of the predetermined parameter hierarchy are weighted, and the method further comprises adjusting weights to generate an updated hospital schedule in response to the detected deviations.

According to another example, adjusting the weights is further based on the hardness quotient.

According to another example, the plurality of personal includes doctors, nurses, technicians, and cleaners.

According to another example, the system controls the medical devices via interfaces to adjust, activate, or deactivate the medical devices as required by the hospital schedule.

According to another example, the system interfaces with software systems to read in and read out data, including procedure information, personnel information, and resource information, for generating the hospital schedule and updating the hospital schedule.

According to another example, the medical devices include robot-assisted surgery systems, standardized tool kits for orthopedics, and implants, and wherein the preparation schedule for the medical devices includes tasks to clean, sterilize, set up, and assess the medical devices based on the surgical schedule that was generated.

According to another example, the hospital schedule includes a sterilization status of each medical device.

According to another example, the procedures include information on the type of intervention, operation steps with duration, personnel requirements and a personnel deployment plan, device requirements and device usage plan, space requirements and room planning.

According to yet another example, a computer-readable medium may comprise program code that, when the program code is executed on a computer, a processor, or a programmable hardware device, performs the method.

According to yet another example, an apparatus for scheduling a plurality of procedures in a hospital, the apparatus may comprise programming instructions, a processor, an interface communicatively coupled to the processor and configured to interface with a network of the hospital. The processor using the interface according to the programming instructions to acquire resource information by monitoring a plurality of hospital resources, wherein the plurality of hospital resources include a plurality of rooms and a plurality of medical devices, obtain procedure information for a plurality of patients, and access personnel information on a plurality of personnel, including qualifications and working hours for each personnel. The processor further using the programming instructions to process the resource information, procedure information, and personnel information to generate one or more hospital schedule using a model based on a predetermined parameter hierarchy, the hospital schedule assigning an at least one room, an at least one medical device, and an at least one personnel for each procedure. Wherein the model is modified based on a hardness quotient. The processor further using the programming instructions to rank the one or more hospital schedules according to the model. The processor further using the interface according to the programming instructions to electronically reserve the rooms and electronically prepare the medical devices based on a ranked hospital schedule.

According to another example, each procedure has a delay probability and wherein the model is further based on the delay probability of each procedure.

According to another example, the plurality of rooms comprises a first room subset and a second room subset and the personnel information comprises a first personnel subset, wherein resource information includes availability information on the first room subset and the second room subset and personnel information comprises availability information on the first personnel subset. Wherein the hardness quotient is between a combination of the availability information for the first room subset and the second room subset and the availability information for the first personnel subset. Wherein the predetermined parameter hierarchy is modified by the hardness quotient.

The planning of operations, the associated personnel deployment planning as well as the planning of the available standing resources, is currently mostly done manually and, if so, only rudimentarily without software. This complex planning poses a high administrative burden workload for medical and nursing staff and often ignores sensor information. In addition, a timely adjustment of the plan is required short-term changes (e.g. a change in surgery order due to a resource failure) is hardly possible.

The method and apparatus are for the automatic assignment of necessary space, personnel, and device/tool resources for a defined set of operations using a model. The model includes algorithms for solving the assignment problem with constraints (e.g. resource availability) in connection with the processing of sensor information from medical technology via interfaces to monitor the condition and availability and control of medical technology via interfaces as well. This includes interfaces to existing software systems (such as a hospital information system (HIS)) for reading in and reading out data. This allows for automated, optimized surgical planning with the option of using different planning scenarios to grasp, realized. The method and apparatus should be able to replan at any time if changes occur (e.g. in the event of a change in the surgical sequence or duration, as well as personnel or equipment failure) to ensure optimal utilization existing capacities can be reached quickly.

BRIEF DESCRIPTION OF THE FIGURES

Some examples of apparatuses and/or methods will be described in the following by way of example only, and with reference to the accompanying figures, in which.

DETAILED DESCRIPTION

Figure 1:
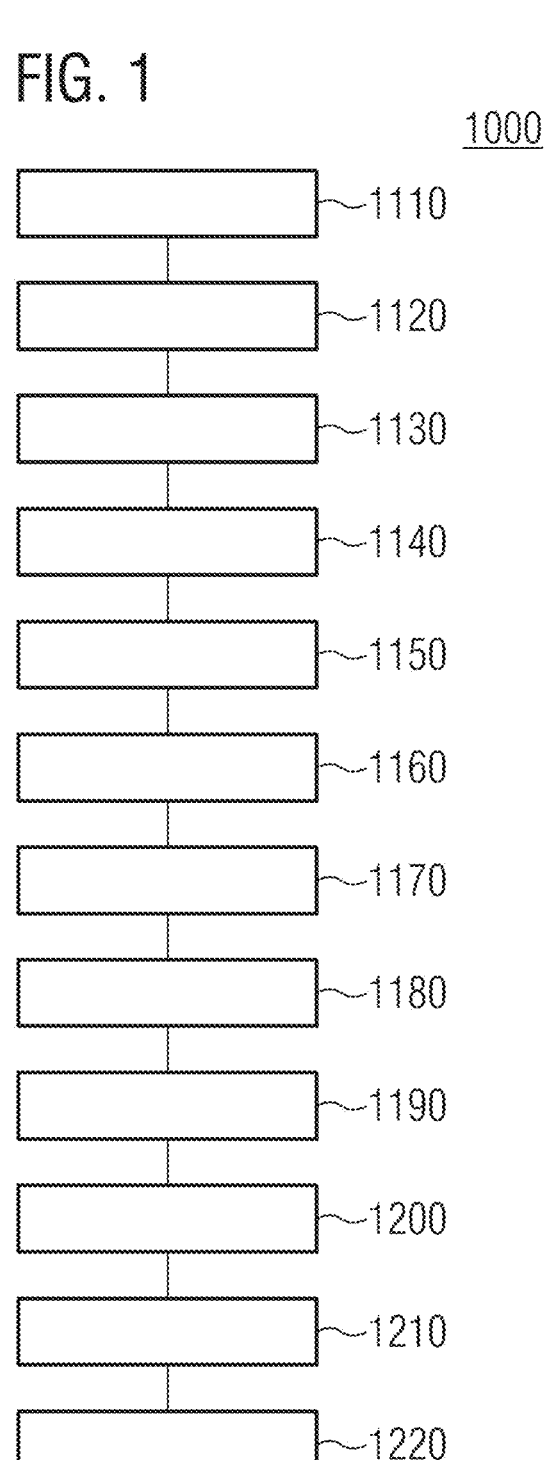
FIG. 1 shows a diagram of a method of scheduling a plurality of procedures in a hospital using a scheduling system.

Some examples are now described in more detail with reference to the enclosed figures. However, other possible examples are not limited to the features of these embodiments described in detail. Other examples may include modifications of the features as well as equivalents and alternatives to the features. Furthermore, the terminology used herein to describe certain examples should not be restrictive of further possible examples.

Throughout the description of the figures same or similar reference numerals refer to same or similar elements and/or features, which may be identical or implemented in a modified form while providing the same or a similar function. The thickness of lines, layers and/or areas in the figures may also be exaggerated for clarification.

When two elements A and B are combined using an "or", this is to be understood as disclosing all possible combinations, i.e. only A, only B as well as A and B, unless expressly defined otherwise in the individual case. As an alternative wording for the same combinations, "at least one of A and B" or "A and/or B" may be used. This applies equivalently to combinations of more than two elements.

If a singular form, such as "a", "an" and "the" is used and the use of only a single element is not defined as mandatory either explicitly or implicitly, further examples may also use several elements to implement the same function. If a function is described below as implemented using multiple elements, further examples may implement the same function using a single element or a single processing entity. It is further understood that the terms "include", "including", "comprise" and/or "comprising", when used, describe the presence of the specified features, integers, steps, operations, processes, elements, components and/or a group thereof, but do not exclude the presence or addition of one or more other features, integers, steps, operations, processes, elements, components and/or a group thereof.

FIG. 1 shows a diagram of a method 1000 of scheduling a plurality of procedures in a hospital using a scheduling system. The scheduling system may include a processor and an interface. The method 1000 includes interfacing 1110 with a network of the hospital to acquire resource information by monitoring a plurality of hospital resources. The plurality of hospital resources may include a plurality of rooms and a plurality of medical devices. The method 1000 further includes obtaining 1120 procedure information for a plurality of patients and accessing 1130 personnel information on a plurality of personnel, including qualifications, and working hours for each personnel.

A hospital network may be a system of interconnected devices or entities that can communicate and share information in a hospital or other setting, often enabling data exchange, collaboration, or resource sharing. This term may be used interchangeably with "hospital information network," which may emphasize the role of data exchange and information management in healthcare settings. It can encompass larger healthcare ecosystems involving multiple hospitals, clinics, and medical providers. A hospital network is a specialized interconnected infrastructure that facilitates communication, data exchange, and resource sharing among various departments, medical devices, personnel, and systems within a hospital or healthcare facility. It enables seamless coordination of healthcare services, patient information management, and the efficient operation of medical equipment. Hospital networks can include wired and wireless connections, data centers, electronic health record systems, and communication protocols, all tailored to support the unique requirements of healthcare delivery.

Hospital resources may encompass the various assets and elements available within a hospital setting to provide healthcare services. This may include medical equipment, personnel, facilities, and supplies. Hospital resources may include operating rooms (e.g. anesthesia; induction and adjustment rooms) and medical devices or tools (e.g. MRI machines, injection devices, robot-assisted surgery systems, standardized tool kits for orthopedics, or implants and display of their sterilization status) and pharmaceuticals (e.g. dispensing and delivery systems).

Resource information may include data or details about the available resources, including their characteristics, availability, and utilization. It may relate to methods or systems for managing and accessing resource-related data. Examples include inventory management systems, energy consumption tracking, and resource allocation algorithms.

Rooms may denote enclosed spaces or compartments within a building, often designed for specific purposes or functions. In a hospital context, rooms can include patient rooms, examination rooms, waiting rooms, anesthesia rooms, and surgical theaters.

Medical devices may be instruments, machines, or tools designed for diagnosing, monitoring, or treating medical conditions. These can range from simple devices like thermometers to complex equipment such as MRI scanners. Examples also include pacemakers, infusion pumps, and X-ray machines.

Hospital procedures may refer to the established protocols or methods followed in a healthcare setting to provide medical care, ensure patient safety, and maintain hospital operations. Examples include infection control procedures, surgical protocols, and emergency response procedures.

Procedure information may involve data or documentation related to specific medical or operational procedures. This can include patient records, surgical logs, and procedural guidelines. It may involve methods for storing, accessing, or analyzing procedure-related data.

Patients may be individuals receiving medical care or treatment within a healthcare facility. They may require various medical interventions and services, and their health information is often documented for treatment purposes. Examples of patients include individuals seeking check-ups, surgery, or ongoing medical management.

In the method 1000, the plurality of personal may include doctors, nurses, technicians, and cleaners. Hospital personnel may include the healthcare professionals and staff members who work within a hospital. This can encompass doctors, nurses, administrative staff, and maintenance workers. In a broader context, it may also involve virtual or remote healthcare personnel.

Personnel information may comprise data and details about the individuals working within an organization or system, often including their personal information, job roles, and qualifications. It may pertain to methods or systems for managing, storing, or accessing information related to personnel. Examples include employee databases, HR management systems, and staff directories.

Personnel qualifications may refer to the skills, training, certifications, and expertise possessed by individuals in a specific profession or job role. The system or algorithms may assess and match personnel qualifications with specific tasks or requirements. Examples include qualification verification systems, skill-matching algorithms, and competency assessment tools.

Working hours may denote the specific time periods during which individuals are expected to be actively engaged in their work or job-related activities. This concept is applicable in various hospital professions and may involve scheduling and time management systems. Examples include shift schedules, employee time-tracking tools, and flexible work hour arrangements.

The method 1000 includes processing 1140 the resource information, procedure information, and personnel information to generate one or more hospital schedules using a model based on a predetermined parameter hierarchy. The hospital schedule may assign or denote an at least one room, an at least one medical device, and an at least one personnel for each procedure.

Calculation of the one or more hospital schedules is based on a model which considers relevant parameters for the hospital. The model may consider parameters such as procedures (e.g. surgeries) and the availability of rooms, doctors, or equipment when developing schedules. The model may also consider factors like scheduling most procedures during a tight window such as working hours (e.g. 08:00 and 18:00) or in a more relaxed window (e.g. until 20:00) that allows more downtime between procedures. The model may consider infectious patients or procedures, particularly in relation to how an infectious environment may delay the use of a room, doctor, or equipment. The model on which calculation of a hospital schedule is based may enable integrating the deviation of a current schedule into an updated schedule ship itinerary such that operation of the hospital may be maintained and that as few delays as possible, or no delays, and/or cancellations in the operation of the hospital.

The model may comprise a set of all surgeries to be planned within a given time frame (e.g. a day, a week, or another period).

$$S = \{1, 2, 3, \dots, |S|\}$$

The model may further comprise a function showing or indicating how infectious a patient or a surgery is:

$$inf_s \in \{0,1,2,\ldots,10\}$$

The model may, first, divide S into two subsets $S_{inf} \cap S_{\overline{inf}} = \emptyset$ where $S_{inf} \leq S$ such that $inf_s > 0$ and where $S_{\overline{inf}} \leq S$ such that $inf_s = 0$.

The model may, second, order items in $S_{inf}$ if $S_{inf} \neq \emptyset$ in a descending way or order according to $inf_s$ and the number of rooms qualified for the surgery in an ascending way or order $|r_s|$.

Let $$f_S = \left| \frac{e_S - b_S}{d_S} \right|$$

be the flexibility factor or the delay probability where $e_s$=end of surgery, $b_s$=beginning of surgery, and $d_s$:=approximated surgery of surgery S.

As a sub step 2a, the model may schedule surgeries with $f_s=1$ by determining the end of the surgery $e_s$ as follows:

$$e_s = \max(e_W d_s; e_W a_s; e_W p_s)$$

Where $e_W d_s$ is the end of the workday for the doctor that is qualified for this surgery. Where $e_W a_s$ is the end of the workday for the anesthesia personal that is qualified for this surgery. And where $e_W p_s$ is the end of the workday for the additional personnel needed for this surgery. A surgery should be assigned to the most preferred or qualified room and broadly best fit the personal, anesthesia or surgery personnel.

As a substep 2b, the model may schedule surgeries with $f_s > 1$ by determining the end of the surgery $e_s$ as follows:

$$e_S := \max(e_W d_S; e_W a_S; e_W p_S) \cdot f_S$$

Where $e_W d_s$ is the end of the workday for the doctor that is qualified for this surgery. Where $e_W a_s$ is the end of the workday for the anesthesia personal that is qualified for this surgery. And where $e_W p_s$ is the end of the workday for the additional personnel needed for this surgery. A surgery should be assigned to the most preferred or qualified room and broadly best fit the personal, anesthesia or surgery personnel.

Figure 3:
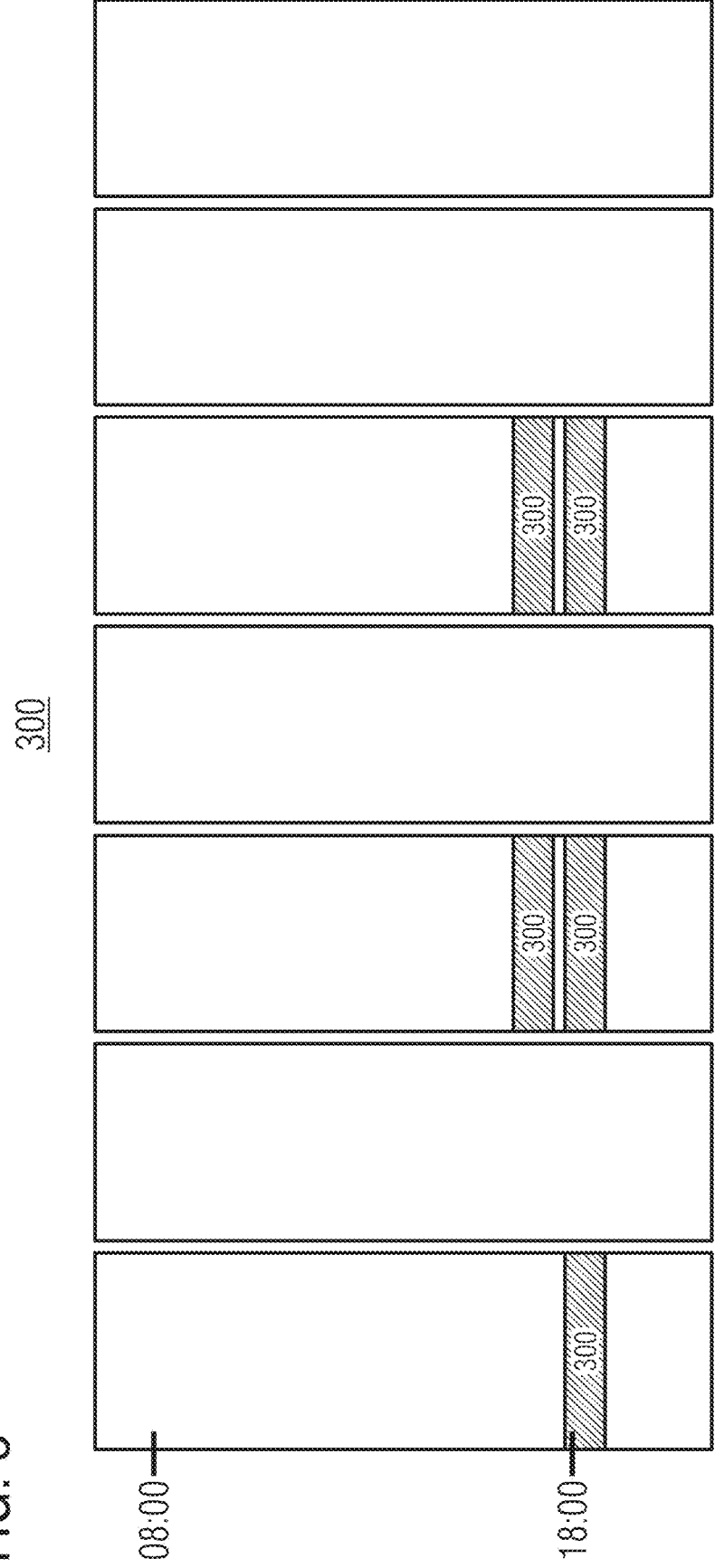
FIG. 3 shows an example of a schedule for surgeries that are infectious.

The model further creates a plan with surgeries that are infectious $S_{inf}$ as input for the planning of surgeries from $S_{\overline{inf}}$. FIG. 3 shows an example of a schedule 300 for surgeries that are infectious 301. Infectious surgeries may be, for example, be planned at the end of the day, reducing a factor for delay in the schedule and increasing outcomes for patients. For example, a room used during an infectious surgery may require extensive decontamination before it is used again, meaning that any further procedures scheduled for that room must wait until the room is ready to be used again or another suitable room becomes available. Moreover, doctors, anesthetists, or other surgery personnel may also require extensive post operation decontamination, delaying their availability for other scheduled surgeries. If the procedure is scheduled near the end of the day, the room and the affected personnel may be disinfected during time outside of operating hours so that their disinfection does not delay other procedures. This may also increase outcomes for patients because their surgeon or other personnel will be less likely to have contacted an infectious patient immediately prior to their own surgery. Likewise their operating room will be less likely to have contained an infectious patient.

The model may, third, take the input of the already planned $S_{inf}$ and order the elements of $S_{\overline{inf}}$ by $|r_s|$ (number of rooms where the surgery can take place) in ascending way or order. Then order for each $|r_s|$ the elements (surgeries) by the ratio between $|a_s|$ number of rooms for anesthesia that are linked to the surgeries rooms $$\frac{|a_S|}{|a_S|} = f_r$$

(room function) in an ascending way or order.

As a sub step 3a, the model may plan the surgeries with $f_s=1$ by duration (shortest first). This creates a list of surgeries that could not be planned $S_{\overline{inf}P1}$. As a substep 3b, the model may plan the surgeries with $f_s > 1$ by duration (shortest first). This creates a list of surgeries that could not be planned $S_{\overline{inf}P2}$.

As a substep 3c, if $S_{\overline{inf}P1} \cup S_{\overline{inf}P2} = \emptyset$ terminate the model. Otherwise, reschedule by following substeps 3a and 3b but by adding the number of free anesthetists at the possible beginning of the surgery minus the timeframe for anesthesia, and sort by this number. As a substep 3d, list the surgeries that could not be planned with the missing resources.

Within this context, in that the operation-relevant parameters are considered, the model may adhere to regulations specific to the medical field and may provide the updated hospital schedule which complies with the regulations specific to the medical field and/or which optionally indicates any occurrence where regulations specific to the medical field would not be complied with. Here, the model is designed, for example, to optimize a hospital schedule to the effect that operation of the hospital is efficiently and safely maintained if any deviations occur. Within this context, the model may be designed, e.g., to at least partly, if possible, allow deviations which are within tolerated deviations of regulations specific to the medical field so as to maintain operation of the hospital and to avoid, delays in procedures. The regulations specific to the medical field may comprise framework conditions within which deviations from regulations are made possible in exceptional situations. For example, generally a doctor of anesthesiology should stay during a whole medical procedure requiring anesthesia. And in some jurisdictions they must remain. However, in other jurisdictions only a nurse anesthetist is required to remain, freeing up a doctor to perform another procedure. In the latter case the model could deviated from the regulation that a doctor should remain if a certified nurse anesthetist is available and an optimized hospital schedule requires the doctor to perform another anesthesia procedure.

It may thus be stated that the method of scheduling a plurality of procedures for a hospital enables optimized, efficient, and safe operation of the hospital while adhering to regulations specific to the medical field and enables facilitated verification of compliance with the regulations specific to the medical field by adapting the schedule to current conditions. Moreover, the method of scheduling procedures may lower cost since the model for calculating the updated schedule may consider regulations specific to the medical field and hospital requirements (e.g. by means of the parameters) and may thus avoid fees or fines arising in the event of non-compliance of the regulations.

Parameters for processing the resource information may include the type of intervention or procedures. From this may be derived the operation steps, personal steps, duration, personnel requirements, personnel deployment plan, device requirements and device usage plan, space requirements and room planning. Additional parameters may comprise machine down-time or personnel rest periods.

The procedure information allows for the model to plan interventions such that no or only minor delays will occur in the operation of the hospital. For example, the method may also consider time for setting up an operation room in the model, as a result of which the updated schedule indicates, in the task schedule for the personnel when and by who operation setup works are ideally to be performed and which medical devices are requires so that the hospital can operate safely and with reduced operational disturbances. Moreover, the model may comprise safety-relevant parameters such as personnel resting periods, for example, which are defined by regulations specific to the medical field and are to be complied with so as to ensure safe operation of the hospital since in the event of non-adherence to the personnel resting periods, overtiredness of the crew may occur, for example, and thus, operation of the hospital will be possible only to a limited extent and regulations specific to the medical field will not be complied with, which may increase cost of operating the ship and may possibly result in accidents.

In accordance with an embodiment, the model is configured to allow, in an exceptional state, deviations from the safety-relevant parameters so as to maintain operation of the hospital. In other words, the model may be designed, e.g., to violate the safety-relevant parameter such as a personnel rest period (e.g. for a nurse or doctor) in an exceptional state so as to maintain operation of the hospital. An exceptional state may include performance of a life-saving surgery by a doctor who has just performed another surgery. Thus, the model may prioritize a necessary surgery and forgo a rest period between surgeries so that the hospital may continue its operation with only minor or no limitations. Likewise, the model may, for example, ascertain an exceptional situation in the event of a delayed start to a procedure, and may thus calculate (e.g. for a doctor who, according to the medical specific regulations, requires a specific rest period) a deviating rest period, which lie within deviations that are tolerated according to the regulations. As a result, the model may assign tasks, within the task schedule, to personnel so that a reduced delayed surgery time may be complied with while all tasks that need to be performed are performed, and so that operation of the hospital is not or hardly delayed. As a result, the hospital schedule is optimized and designed to be very efficient.

A model is not a perfect schedule solver. The algorithm of the model converges with reduced parameter space. This reduces computation time and allows for real-time replanning without computing a massive problem space. The real-time replanning of a hospital schedule may be important in emergency situations, such as a mass casualty event, that requires considerable hospital resources in a short time. The model may evaluate many feasible solutions or may optimize existing schedules faster than current solutions provide.

In accordance with an embodiment, calculation of the hospital schedule on the basis of the model may be effected within less than five minutes. In accordance with an embodiment, the time period may also be less than a minute, 30 seconds or one second, as a result of which the schedule may be, e.g., dynamically adapted in real time to the updated ship itinerary. Thus, the method may react very quickly to deviations of the current schedule and may thus ensure efficient and safe operation of the hospital at any point in time during its operation.

The model may be modified based on a hardness quotient. A hardness quotient may denote a measure of the model's adaptability and flexibility. This metric may reflect the model's ability to produce adaptable schedules for specific parameters determined as a priority to the hospital. A low hardness quotient may signify that the model is more versatile and capable of adapting to various inputs and scenarios. It may signify the model's capacity to provide meaningful responses or solutions across a spectrum of tasks, showcasing its flexibility and versatility in different applications. A high hardness quotient may indicate that specific factors like workhours or room availability are not flexible and must be honored when creating a hospital schedule. A high hardness quotient implies more parameter tuning. The model internally searches for already known structures and properties and compares more solutions.

For example, if a surgery must be planned or cannot be performed as planned the model may mainly account for the availability of a suitable room. In situations where many rooms are suitable or many timeslots are available (e.g. many degrees of freedom exist), the hardness quotient may be used to narrow down the world of possibilities by encouraging the prioritization of other factors.

Considering timeslot or availability information of personnel in the model implies that if the person is free at those timeslots they reduce the timeslots. A hardness quotient may include factors such as delay probability in procedures. This may be considered for certain procedures or personnel that are more likely to exceed a designated timeslot and thus require special consideration when building the schedule compared to a general rule. More well know procedures or experienced practitioners may better adhere to the time slot whereas complex procedures or inexperienced practitioners may increase delay probability.

A hardness quotient may also consider practitioner or personnel preferences. If a practitioner prefers morning verses evening procedures, extended breaks between procedures, or specific rooms for procedures, these preferences may reduce the pool of possibilities when forming a schedule and narrow down a list of possible schedules to those that may be most preferred based on certain preferences.

Generally, when considering multiple dimensions of the scheduling model the availability of personnel, the time of a procedure, and the delay probability of the procedure may depend on each other more heavily than room availability. As many rooms tend to be suitable or reconfigurable for many procedures. The calculation of hospital schedules becomes difficult as options increase. However, hospital scheduling must be done and redone in real-time to avoid delaying procedures. Therefore, using a model constraint by a hardness question may allow for the calculation of a near-optimal schedule within in a proper time so that time slots do not shift (or do not drastically shift) while the schedule is being calculated.

Time sensitivity underscores the importance of efficient schedule, which can vary depending on individual hospital requirements. A model must consider the work hours and other time factors impacting surgery teams comprised of surgeons, specialized nurses, and general care nurses. The model must also consider the impact of other personnel such as cleaning staff. The scheduling of dedicated cleaning staff is of paramount importance in a hospital as it ensures the maintenance of a hygienic and safe environment, allowing for the smooth and timely execution of procedures while minimizing infection risks.

The proposed approach introduces variability in generating proposals, seeking the best three solutions that meet all constraints. A model may depend on the weighting of each parameter, dependent on each hospital and its individual requirements.

The method 1000 includes ranking 1150 the one or more hospital schedules according to the model interfacing 1160 with the network of the hospital to electronically reserve the rooms and electronically prepare the medical devices based on a ranked hospital schedule.

Raking hospital schedules may allow for better optimization, as it considers multiple options, potentially identifying more efficient or resource-saving schedules. It may also accommodate diverse preferences and constraints, catering to individual, hospital, or system wide needs or specific requirements. Additionally, ranking provides flexibility in adjusting schedules over time, ensuring adaptability to changing circumstances or priorities. Further, it promotes transparency and informed decision-making by presenting a range of alternatives, enhancing the overall quality of scheduling outcomes.

Ranked schedules should meet all constraints of the model. Generally they may be ordered according to the result of the model, where more optimal schedules are presented above less optimal. However, they may also be weighted based on hospital parameters. This may be done after the model is finished as a penalty so that optimal schedules are rearranged based on specific hospital desires. For, example if an optimal schedule complies less well with regulations than a sub-optimal schedule it may be penalized in a ranking. Rankings may also be used as a tie-breaking mechanism, where to identical optimal schedules are sorted based on a factor that is not used in the model. For example, in a hospital seeing to maximize their budget, two optimal schedules may be ordered based on revenue generated by certain procedures (e.g. knee operations).

The method 1000 may further include presenting 1700 the one or more hospital schedules to a user, wherein the ranked hospital schedule is selected by the user. Present many solutions to a user allows the hospital planner to choose an individualized schedule that includes factors only privy to the user.

In the method 1000, each procedure may have a delay probability and wherein the model is further based on the delay probability of each procedure. Further, the procedure information may include a timeslot parameter for each procedure and the delay probability alters the timeslot parameter of each procedures. Timeslot parameters can be generalized for the procedure or individualized depending on an estimate due to the individual complexity of the procedure or experience of a practitioner. An increased delay probability may lead to increased timeslots in the schedule. When the model is computed, increased timeslots may directly lead to increased optimization opportunities and schedule possibilities.

Including a delay probability into each procedure may improve the scheduling mode by providing more accurate estimates of procedure timing and reducing the need to refactor a schedule when a procedure is delayed. This may lead to optimized staffing, improved workflow efficiency, and potential cost reductions. Moreover, the model may be designed to anticipate and adapt to potential delays bolsters patient safety and enhances compliance with relevant regulatory standards.

The hardness quotient of method 1000 may modify the model to produce one or more hospital schedules with increased availability parameters. Producing hospital schedules with increased availability allows for schedules that are more flexible and do not have to be updated when a procedures is delayed or a resource is unavailable.

In the method 1000, a plurality of rooms may include a first room subset and a second room subset and plurality of personnel comprises a first personnel subset. Resource information may include availability information on the first room subset and the second room subset and personnel information comprises availability information on the first personnel subset. The hardness quotient may be determined to be between a combination of the availability information for the first room subset and the second room subset and the availability information for the first personnel subset. The predetermined parameter hierarchy may be modified by the hardness quotient. A subset of rooms or personnel may be the limiting factor in optimizing a schedule. Therefore the availability of a first subset of rooms or personnel may determine how tightly the model is constrained.

In the method 1000, the plurality of rooms may include anesthesia induction rooms and wherein the plurality of personnel comprises anesthetists. The hardness quotient may include a ratio between the availability information on a plurality of further rooms and the anesthesia induction rooms or anesthetists.

The allocation of anesthesia resources among surgeries is a common challenge. Anesthesiologists are a common resource that may be divided among all surgeries so their availability may constrain the model more than other factors. Similarly, anesthesia rooms may be another limiting factor. Although, the use of an anesthesia room is not a must, as anesthesia can may also be done in a surgery room in order to optimize a more degree of freedom in the model In the method 1000, the first room subset may be operating rooms, the second room subset may be anesthesia induction rooms, and the first personnel subset may be anesthetists. In certain hospitals or scenarios, the limiting rooms may be other additional rooms, such as operating rooms, rather than or in addition to anesthesia.

The method 1000 may further include interfacing 1180 with the network of the hospital to acquire updated resource information by monitoring the plurality of hospital resources to detect conflicts between the hospital schedule and the plurality of hospital resources. The method further may compare 1190 the hospital schedule with the updated resource information to detect deviations between the hospital schedule and the hospital resources and generate 1200 an updated hospital schedule in response to the detected deviations. The updated hospital schedule may be generated using the model. The method 1000 may further include interfacing 1210 with the network of the hospital to electronically reserve the rooms and electronically prepare the medical devices based on the updated hospital schedule. In the method 1000, the system may control the medical devices via interfaces to adjust, activate, or deactivate the medical devices as required by the hospital schedule. In the method 1000, the system may interface with software systems to read in and read out data, including procedure information, personnel information, and resource information, for generating the hospital schedule and updating the hospital schedule.

The automated interfacing with hospital resources to extract information about rooms and orchestrate medical device setup according to a predefined schedule, yields substantial advantages over current methods. Direct interfacing significantly enhances scheduling efficiency by auto-mating resource access, thereby reducing manual adminis-trative overhead, and ensuring optimal allocation of resources, including rooms and medical devices. This streamlined automation not only improves patient safety by minimizing errors in resource setup but also diminishes the likelihood of scheduling delays due to resource unavailabil-ity. For example, directly interfacing with a drug delivery robot according to an schedule may allow for automated delivery of medication to an operating room as part of a preparation procedures. It may allow for the patients' iden-tity, medication, and dosage to be automatically conformed and safely transported to the designated patient's location. This automated process enhances the accuracy and effi-ciency of medication administration while maintaining a detailed record of the delivery for medical staff and patient records.

In the method 1000, the medical devices may include robot-assisted surgery systems, standardized tool kits for orthopedics, and implants. The preparation schedule for the medical devices may include tasks to clean, sterilize, set up, and assess the medical devices based on the surgical sched-ule that was generated. For example, the direct interface with an MRI machine may allow for the activation and configuration of the machine, ensuring the appropriate set-tings are in place for the specific scan ordered, and signaling the readiness of the machine for the medical staff to proceed with the procedure. This automation streamlines the process, reduces the risk of human error, and optimizes the utilization of the MRI machine. And generally, interfacing directly with medical devices may further contributes to cost savings through efficient resource utilization and offers transparency in data management, thus promoting data-driven decision-making and resource planning. Additionally, the innovation facilitates adaptability to real-time scheduling changes and adherence to regulatory standards, underscoring its capacity to enhance healthcare operations. Furthermore, the auto-mated interfacing ensures precise data accuracy, supporting compliance with established procedures and regulatory requirements, fostering workflow efficiency, and alleviating manual resource setup burdens.

In the method 1000, the hospital schedule may comprise a task schedule for the personnel and a preparation schedule for the rooms and medical devices. Rooms may have devices dedicated to that room or preexisting in that room in some scenarios whereas, in others, rooms may have to be prepared with the appropriate device, adding time to the schedule produced by the model. Preparing such rooms or devices may have various tasks involved with multiple, possibly timed, tasks for each room or device. In accordance with an embodiment, the model may consider whether tasks of the task schedule for the hospital personnel may be temporally split up and/or be split up among several personnel. Con-sequently, when the deviations indicate that urgent tasks need to be accomplished now and cannot be postponed, e.g., to a later point in time, the model may, e.g., postpone other simultaneous tasks, according to the task schedule of the hospital itinerary, to a different point in time or split them up among other personnel members. Thus, activities that result from the deviations may be performed without any or with only minor restrictions of the operation of the hospital. Thus, the method can assign task and activities to personnel on the basis of the model, with the updated schedule, and can determine when they are to be performed. In this manner, optimized, efficient and safe operation of the hospital can be ensured.

In the method 1000, the predetermined parameter hierar-chy may include patient priority parameters, resource avail-ability parameters, and personnel availability parameters. The model may be further based on maintenance times for the medical devices so that the preparation schedule for the equipment indicates maintenance times. The model may be further still based on working hours for the personnel so that the task schedule for the personnel indicates working hours. The factors the hardness quotient might not be equal and be ranked according to a hierarchy. For example, complying with medical regulations may be ranked higher than afford-ing long break times between procedures or scheduling personnel to a confined location instead of in locations throughout the hospital.

In the method 1000, the parameters of the predetermined parameter hierarchy may be weighted, and the weights may be adjusted 1220 to generate an updated hospital schedule in response to the detected deviations. Weights allow the differences between parameters to be better defined. For example, resource availability parameters may be weighted several times greater than patient priority preferences. Thus ensuring that most proposed hospital schedules ensure resource availability.

In the method 1000, adjusting the weights 1220 may be further based on the hardness quotient. Weights of param-eters may be dynamically adjusted in order to better satisfy the hardness quotient. For example, if a tight hardness quotient is reducing the set of proposed schedules or increas-ing computation time, the weight of preferences informing the model can be adjusted to produce more results. Likewise a loose hardness quotient could increase the weights of prioritized parameters to reduce the computation space and produce results faster.

In the method 1000, the hospital schedule may include a sterilization status of each medical device. Determining sterilization status may allow for the activation of self-sterilization or the scheduling of cleaners to sterilize medical devices.

In the method 1000, procedures may include information on the type of intervention, operation steps with duration, personnel requirements and a personnel deployment plan, device requirements and device usage plan, space require-ments and room planning. The more information known about procedures could better divide the scheduling space into specific tasks and assignments. In complicated proce-dures, this may allow for the specific assignment of special-ists during time periods that do not span the entire proce-dure. For example an anesthesiologist might not be required to stay the full length of a procedure if a nurse is available, allowing the doctor to perform other procedures during the duration of the first procedure.

Figure 2:
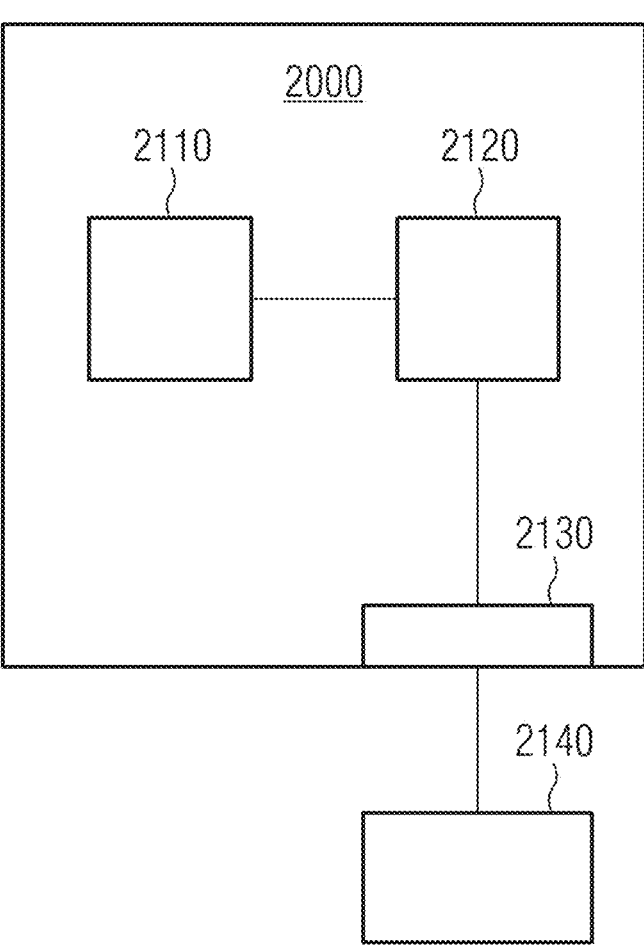
FIG. 2 shows a schematic of an apparatus for scheduling a plurality of procedures in a hospital using a scheduling system.

FIG. 2 shows a schematic of an apparatus 2000 for scheduling a plurality of procedures in a hospital. The apparatus may comprise programming instructions 2110, a processor 2120, and an interface 2130 communicatively coupled to the processor 2120 and configured to interface with a network 2140 of the hospital. The processor 2120 using the interface 2130 according to the programming instructions 2110 to acquire resource information by moni-toring a plurality of hospital resources, wherein the plurality of hospital resources include a plurality of rooms and a plurality of medical devices, obtain procedure information for a plurality of patients, and access personnel information on a plurality of personnel, including qualifications and working hours for each personnel.

The processor 2120 further using the programming instructions 2110 to process the resource information, procedure information, and personnel information to generate one or more hospital schedule using a model based on a predetermined parameter hierarchy, the hospital schedule assigning an at least one room, an at least one medical device, and an at least one personnel for each procedure, wherein the model is modified based on a hardness quotient; and rank the one or more hospital schedules according to the model.

The processor 2120 further using the interface 2130 according to the programming instructions 2110 to electronically reserve the rooms and electronically prepare the medical devices based on a ranked hospital schedule.

In the apparatus 2000, each procedure may have a delay probability and wherein the model is further based on the delay probability of each procedure.

In the apparatus 2000, the plurality of rooms may include a first room subset and a second room subset and the personnel information comprises a first personnel subset, wherein resource information includes availability information on the first room subset and the second room subset and personnel information comprises availability information on the first personnel subset, wherein the hardness quotient is between a combination of the availability information for the first room subset and the second room subset; and the availability information for the first personnel subset, wherein the predetermined parameter hierarchy is modified by the hardness quotient.

The aspects and features described in relation to a particular one of the previous examples may also be combined with one or more of the further examples to replace an identical or similar feature of that further example or to additionally introduce the features into the further example.

Examples may further be or relate to a (computer) program including a program code to execute one or more of the above methods when the program is executed on a computer, processor, or other programmable hardware component. For example, there may be a non-transitory, computer-readable medium including program code that, when the program code is executed on a computer, a processor, or a programmable hardware device, performs the method of scheduling a plurality of hospital procedures. Thus, steps, operations, or processes of different ones of the methods described above may also be executed by programmed computers, processors, or other programmable hardware components. Examples may also cover program storage devices, such as digital data storage media, which are machine-, processor- or computer-readable and encode and/or contain machine-executable, processor-executable, or computer-executable programs and instructions. Program storage devices may include or be digital storage devices, magnetic storage media such as magnetic disks and magnetic tapes, hard disk drives, or optically readable digital data storage media, for example. Other examples may also include computers, processors, control units, (field) programmable logic arrays ((F)PLAs), (field) programmable gate arrays ((F)PGAs), graphics processor units (GPU), application-specific integrated circuits (ASICs), integrated circuits (ICs) or system-on-a-chip (SoCs) systems programmed to execute the steps of the methods described above.

It is further understood that the disclosure of several steps, processes, operations, or functions disclosed in the description or claims shall not be construed to imply that these operations are necessarily dependent on the order described, unless explicitly stated in the individual case or necessary for technical reasons. Therefore, the previous description does not limit the execution of several steps or functions to a certain order. Furthermore, in further examples, a single step, function, process, or operation may include and/or be broken up into several sub-steps, -functions, -processes or -operations.

If some aspects have been described in relation to a device or system, these aspects should also be understood as a description of the corresponding method. For example, a block, device or functional aspect of the device or system may correspond to a feature, such as a method step, of the corresponding method. Accordingly, aspects described in relation to a method shall also be understood as a description of a corresponding block, a corresponding element, a property or a functional feature of a corresponding device or a corresponding system.

The following claims are hereby incorporated in the detailed description, wherein each claim may stand on its own as a separate example. It should also be noted that although in the claims a dependent claim refers to a particular combination with one or more other claims, other examples may also include a combination of the dependent claim with the subject matter of any other dependent or independent claim. Such combinations are hereby explicitly proposed, unless it is stated in the individual case that a particular combination is not intended. Furthermore, features of a claim should also be included for any other independent claim, even if that claim is not directly defined as dependent on that other independent claim.

What is claimed is:

1. A method of scheduling a plurality of procedures in a hospital using a scheduling system comprising a processor and an interface, the method comprising:

interfacing with a network of the hospital to acquire resource information by monitoring a plurality of hospital resources, wherein the plurality of hospital resources include a plurality of rooms and a plurality of medical devices;

obtain procedure information for a plurality of patients; and access personnel information on a plurality of personnel, including qualifications and working hours for each personnel;

processing the resource information, procedure information, and personnel information to generate a hospital schedule using a model based on a predetermined parameter hierarchy, the hospital schedule assigning an at least one room, an at least one medical device, and an at least one personnel for each procedure, wherein the model is modified based on a hardness quotient, wherein the hardness quotient represents a ratio of availability between different subsets of the hospital resources, wherein weights of parameters in the predetermined parameter hierarchy are adjusted based on the hardness quotient to reduce a parameter space of the model, thereby reducing computation time for generating the hospital schedule;

interfacing with the network of the hospital to acquire updated resource information by monitoring the plurality of hospital resources to detect a conflict between the hospital schedule and the plurality of hospital resources; and in response to detecting the conflict, automatically generating an updated hospital schedule using the model to resolve the conflict.

2. The method of claim 1, wherein processing the resource information, procedure information, and personnel information generates one or more hospital schedules, the method further comprising:

ranking the one or more hospital schedules according to the model;

presenting the one or more hospital schedules to a user;

receiving a user selection of a ranked hospital schedule from the one or more hospital schedules.

3. The method of claim 1, wherein each procedure has a delay probability and wherein the model is further based on the delay probability of each procedure.

4. The method of claim 3, wherein the procedure information comprises a timeslot parameter for each procedure and the delay probability alters the timeslot parameter of each procedures.

5. The method of claim 1, wherein the hardness quotient modifies the model by adjusting the weights to prioritize availability parameters thereby producing a hospital schedule with increased availability parameters that accommodate delayed procedures or unavailable resources.

6. The method of claim 5, wherein the plurality of rooms comprises a first room subset and a second room subset and plurality of personnel comprises a first personnel subset, wherein resource information includes availability information on the first room subset and the second room subset and personnel information comprises availability information on the first personnel subset, wherein the hardness quotient is between a combination of the availability information for the first room subset and the second room subset; and the availability information for the first personnel subset, wherein the predetermined parameter hierarchy is modified by the hardness quotient.

7. The method of claim 6, wherein the first room subset is operating rooms, the second room subset is anesthesia induction rooms, and the first personnel subset is anesthetists.

8. The method of claim 1, wherein the plurality of rooms comprises anesthesia induction rooms and wherein the plurality of personnel comprises anesthetists, wherein the hardness quotient comprises a ratio between the availability information on a plurality of further rooms and the anesthesia induction rooms or anesthetists.

9. The method of claim 1, further comprising:

interfacing with the network of the hospital to electronically reserve the rooms and electronically prepare the medical devices based on the hospital schedule or the updated hospital schedule.

10. The method of claim 1, wherein the hospital schedule comprises a task schedule for the personnel and a preparation schedule for the rooms and medical devices.

11. The method of claim 10, wherein, predetermined parameter hierarchy includes patient priority parameters, resource availability parameters, and personnel availability parameters;

wherein the model is further based on maintenance times for the medical devices so that the preparation schedule for the equipment indicates maintenance times; and wherein the model is further based on working hours for the personnel so that the task schedule for the personnel indicates working hours.

12. The method of claim 11, wherein the parameters of the predetermined parameter hierarchy are weighted, and the weights are adjusted to generate an updated hospital schedule in response to the detected conflict.

13. The method of claim 12, wherein adjusting the weights is further based on the hardness quotient.

14. The method of claim 1, wherein the plurality of personnel includes doctors, nurses, technicians, and cleaners.

15. The method of claim 1, wherein the system controls the medical devices via interfaces to adjust, activate, or deactivate the medical devices as required by the hospital schedule.

16. The method of claim 1, wherein the system interfaces with software systems to read in and read out data, including procedure information, personnel information, and resource information, for generating the hospital schedule and updating the hospital schedule.

17. The method of claim 1, wherein the medical devices include robot-assisted surgery systems, standardized tool kits for orthopedics, and implants, and wherein the preparation schedule for the medical devices includes tasks to clean, sterilize, set up, and assess the medical devices based on the surgical schedule that was generated.

18. The method of claim 1, wherein the hospital schedule includes a sterilization status of each medical device.

19. The method of claim 1, wherein procedures include information on the type of intervention, operation steps with duration, personnel requirements and a personnel deployment plan, device requirements and device usage plan, space requirements and room planning.

20. A non-transitory, computer-readable medium comprising program code that, when the program code is executed on a computer, a processor, or a programmable hardware device, performs the method of claim 1.

21. An apparatus for scheduling a plurality of procedures in a hospital, the apparatus comprising:

programming instructions;

a processor;

an interface communicatively coupled to the processor and configured to interface with a network of the hospital;

programming instructions configured to cause the processor, using the interface, to the programming instructions to:

acquire resource information by monitoring a plurality of hospital resources, wherein the plurality of hospital resources include a plurality of rooms and a plurality of medical devices, obtain procedure information for a plurality of patients, and access personnel information on a plurality of personnel, including qualifications and working hours for each personnel;

process the resource information, procedure information, and personnel information to generate a hospital schedule using a model based on a predetermined parameter hierarchy, the hospital schedule assigning an at least one room, an at least one medical device, and an at least one personnel for each procedure, wherein the model is modified based on a hardness quotient, wherein the hardness quotient represents a ratio of availability between different subsets of the hospital resources, wherein weights of parameters in the predetermined parameter hierarchy are adjusted based on the hardness quotient to reduce a parameter space of the model, thereby reducing computation time for generating the hospital schedule; and acquire updated resource information by monitoring the plurality of hospital resources to detect a conflict between the hospital schedule and the plurality of hospital resources; and in response to detecting the conflict, automatically generate an updated hospital schedule using the model to resolve the conflict.

22. The apparatus of claim 21, wherein each procedure has a delay probability and wherein the model is further based on the delay probability of each procedure.

23. The apparatus of claim 21, wherein the plurality of rooms comprises a first room subset and a second room subset and the personnel information comprises a first personnel subset, wherein resource information includes availability information on the first room subset and the second room subset and personnel information comprises availability information on the first personnel subset, wherein the hardness quotient is between a combination of the availability information for the first room subset and the second room subset; and the availability information for the first personnel subset, wherein the predetermined parameter hierarchy is modified by the hardness quotient.

\* \* \* \* \*